United States Patent [19]
Taheri

[11] Patent Number: 5,634,935
[45] Date of Patent: Jun. 3, 1997

[54] BALLOON DISSECTION INSTRUMENT AND METHOD OF DISSECTION

[76] Inventor: Syde A. Taheri, 268 Dan Troy, Williamsville, N.Y. 14221

[21] Appl. No.: 490,908

[22] Filed: Jun. 16, 1995

[51] Int. Cl.$^6$ ............................................ A61B 17/00
[52] U.S. Cl. ........................... 606/190; 606/198; 604/96
[58] Field of Search .................................. 606/190, 191, 606/192, 198, 194; 604/96; 600/207; 128/898

[56] References Cited

U.S. PATENT DOCUMENTS

| | | | |
|---|---|---|---|
| 3,039,468 | 6/1962 | Price | 604/49 |
| 5,061,240 | 10/1991 | Cherian | 606/194 |
| 5,197,971 | 3/1993 | Bonutti | 606/192 |
| 5,295,994 | 3/1994 | Bonutti | 606/192 |
| 5,464,394 | 11/1995 | Miller et al. | 606/194 |

FOREIGN PATENT DOCUMENTS

| | | | |
|---|---|---|---|
| WO94/16633 | 8/1994 | WIPO | 606/194 |

*Primary Examiner*—Guy V. Tucker
*Assistant Examiner*—Patrick W. Rasche
*Attorney, Agent, or Firm*—Bilicki & Simpson, P.C.

[57] ABSTRACT

This invention relates to a method for the dissection of blood vessels, lymph nodes and other body organs from the surrounding tissue and to a novel balloon dissection instrument for use in the method. The dissection instrument comprises an elongated tube having at least one inflatable balloon attached around the outer wall of a distal portion of the tube. The method of dissecting a vein, such as the saphenous vein, involves severing of the vein at two sites, defining the length of vein to be dissected. The vein is then accessed by securing the severed end, for example by a thread attached thereto and passed through the lumen of the dissection instrument to serve as a controllable anchor. The distal end of the dissection instrument, with the balloon deflated, is placed over the free end of the vein so that the vein enters the lumen of the instrument and the distal end of the instrument is pressed between the outer layer of the vein, i.e., the adventitia, and the connected fascia. The balloon is then inflated causing the adventitia and fascia to separate in the region proximate to the distal end of the instrument. The balloon is then deflated and the instrument moved forward to encompass the dissected portion of vein within the lumen of the instrument. The balloon is again inflated to free another section of the vein from the surrounding fascia. The procedure is repeated and the instrument advanced along the length of the vein until the desired length of vein has been dissected.

13 Claims, 2 Drawing Sheets

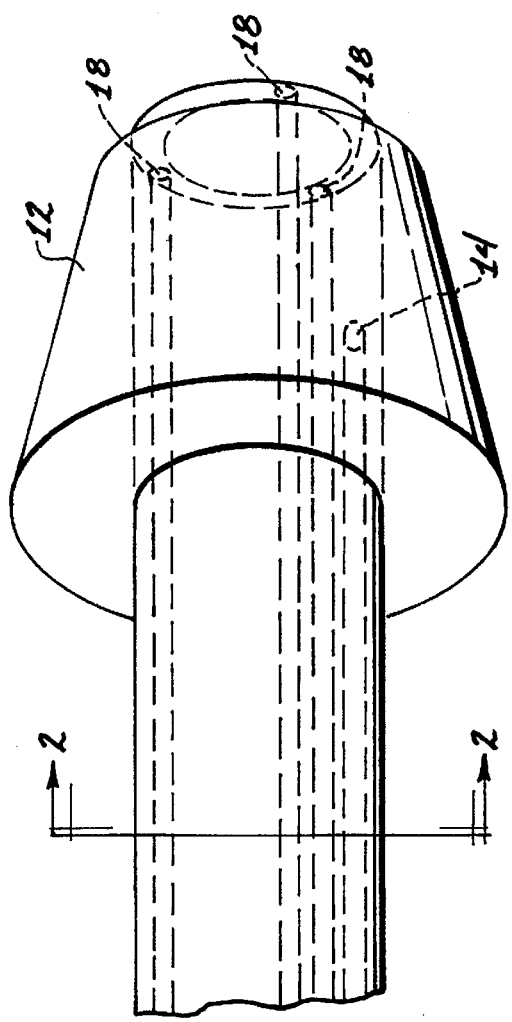
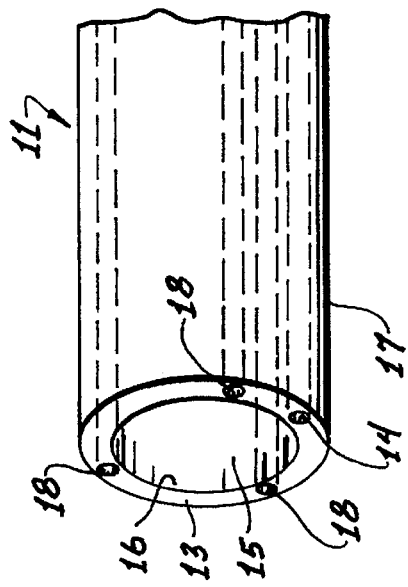
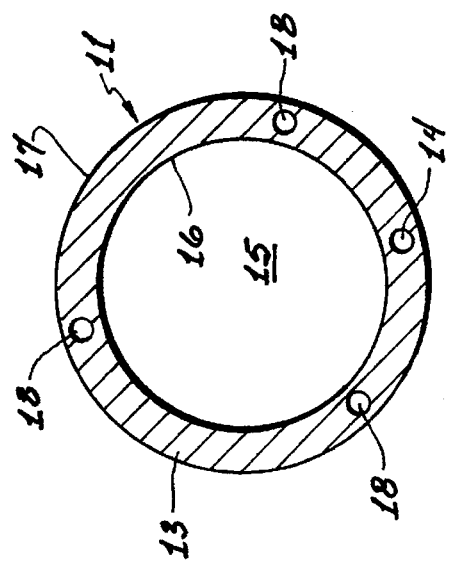
Fig. 1
Fig. 2

BALLOON DISSECTION INSTRUMENT AND METHOD OF DISSECTION

BACKGROUND OF THE INVENTION

This invention relates to a method and apparatus for the dissection of body organs, such as blood vessels, from the surrounding tissues.

The removal of veins, particularly the long or short saphenous vein, can be accomplished by stripping, in a known manner that allows a vein to be removed through two small incisions. In one such stripping method, for example, a cut end of the vein is tied and the vein extracted by invagination. Such methods minimize surgical trauma and provide a favorable cosmetic effect by minimizing the number and size of the incisions and resultant scars. However, the usual object of conventional stripping methods is the removal of the vein without consideration to trauma to the vein itself. Thus, veins removed by conventional stripping methods are generally unsuitable for subsequent use such as implantation in connection with an arterial bypass procedure.

When a vein, or a section of a vein is to be harvested for use in another part of a patient's body, for example, in an arterial bypass, considerable care must be taken in the dissection of the vein. The conventional procedure for the dissection of a blood vessel to be harvested involves the need for multiple incisions including an incision along the entire length of the vein to be dissected, as well as cutting or tearing to separate the adventitia of the vein from the surrounding fascia. In addition to the surgical trauma involved, the resultant scars are generally disfiguring. This is a particular problem for patients whose scars tend to develop hyperpigmentation or keloidal changes.

It is an object of the present invention to provide a method and apparatus that will facilitate the dissection of body organs, such as blood vessels, with a minimum of surgical trauma and disfiguring scars. It is a further object to provide an improved method and apparatus for the dissection of a vein or vein segment that minimizes trauma to the vein itself so that the dissected vein or vein segment is suitable for harvesting and re-use.

SUMMARY OF THE INVENTION

This invention is directed to a novel method and apparatus for the dissection of body organs such as blood vessels, lymph nodes or other body organs or tissues and, in particular, the dissection of veins to be harvested for subsequent use.

The novel apparatus of this invention is a balloon dissection instrument comprising:

an elongated tube comprising cylindrical wall having an outer surface and an inner surface defining a central lumen;

an inflatable/deflatable balloon attached to the tube, surrounding the outer surface of a distal portion of the tube;

at least one inflation conduit extending axially along the length of the tube within the wall between the outer surface and the inner surface thereof and in fluid communication with the interior of the balloon.

In practice, a controllable fluid source is fluidly coupled to the inflation conduit(s), for inflating and deflating the balloon by controlled transmission of fluid pressure. Fluids suitable for inflating the balloon include both liquids and gases.

In a preferred embodiment, the balloon dissection instrument of this invention additionally comprises one or more multi-purpose conduits extending axially along the length of the tube and adapted to accommodate various surgical accessory devices. The multi-purpose conduit provides a passage whereby a removable surgical accessory device can be introduced into the opening of the multi-purpose conduit at the proximal end of the instrument, through the conduit(s) to the opening at the distal end thereof for access to the region of dissection while the controlling means for the surgical accessory device may be connected at the proximal end.

Among the surgical accessory devices that may be introduced through the multi-purpose conduit(s) are: a length of tubing for dispensing or withdrawing fluid to or from the region being dissected; a fiber optic illuminating and visualization device; a fiber optic laser beam energy transmitting device; forceps; a surgical cutting instrument; and the like. The length of tubing for dispensing or withdrawing fluid may be used for various purposes, for example, for the introduction of liquids for irrigation purposes; or for the introduction of medicants; or as a gas conduit for the injection of gas to the dissection site or region of dissection; or for the removal by suction of fluids from the region of dissection. A length of tubing having a suction means attached thereto may be introduced through a multi-purpose conduit for the removal of fluids, including the removal of excess gas from the region of dissection.

The introduction of inert gas through the multi-purpose conduits represents a preferred embodiment of the invention wherein the multi-purpose conduits serve as gas conduits through which the force of a stream or jets of inert gas may be applied, for example during dissection to the juncture of the tissues being separated, to aid in the separation thereof. The inert gas is preferably $CO_2$, however, other inert gases, such as, helium, nitrogen or the like may be employed, if desired. The inert gas may be transmitted through a length of tubing functioning as a surgical accessory located within a multi-purpose (gas) conduit or the gas may be transmitted directly through the gas conduit itself. In either instance, the gas is supplied by controllable gas supply means fluidly coupled to the length of tubing or the multi-purpose conduit.

The method of dissection of a blood vessel, such as a vein segment, using the novel balloon dissection instrument, in accordance with the invention, comprises the steps of a) severing of a vein at an entry site to provide a first end of the vein segment to be dissected;

b) securing the first end of the severed vein segment to be dissected;

c) placing the distal end of the balloon dissection instrument, over the first end of the vein segment causing the vein segment to enter the lumen of the dissection instrument and the distal end of the dissection instrument to be pressed between the adventitia of the vein segment and the surrounding fascia;

d) inflating the balloon to cause the adventitia and fascia to separate in the region around the distal end of the dissecting instrument and free a portion of vein, from the surrounding fascia;

e) deflating the balloon and advancing the instrument along the outer adventitial surface of the vein segment to encompass the freed portion of vein within the lumen of the instrument;

f) repeating the procedure of steps d) and e) until the entire vein segment has been dissected.

In a preferred embodiment, the method of dissection, using a balloon dissection instrument, may be supplemented with the concurrent application of a stream of inert gas to impinge at the juncture of the adventitia and fascia with sufficient force to separate the tissues. The stream of gas may transmitted directly through a gas conduit in the wall of the elongated tube to the distal end of the balloon dissection instrument or through a removable length of tubing inserted through the gas conduit to the distal end. The inert gas, such as $CO_2$, is supplied from a suitable source in fluid communication with the gas conduit or the length of tubing through which the gas is transmitted.

The dissection and removal of a blood vessel involves not only separation from the surrounding fascia, but also separation from connecting branches or other tributary vessels that may be a part of the network to which the blood vessel relates. If a sufficiently long segment of a blood vessel is to be dissected, branches of the blood vessel may be encountered and may have to be severed and tied off before proceeding with the dissection. Thus, for example, the dissection of a saphenous vein may require the cutting and closing of various branch veins, such as perforator veins that enter at various sites along the length of the saphenous vein. When a tributary vein is encountered by the advancing dissection instrument, a percutaneous incision may be made and the tributary vein separated and tied off.

It will be understood that, although the invention has, for convenience, been described with respect to a preferred embodiment, that is, the dissection of blood vessels, especially veins, the use of the method and apparatus for the dissection of other body vessels or organs, and the like, is contemplated within the scope of the invention.

The method and apparatus of this invention may be used in combination with various other method and devices. Thus, for example, the location of branches, such as perforator veins, as well as the movement of the dissection instrument along the dissection path, may be visualized and tracked with the aid of venographic techniques.

In a preferred embodiment of the method of this invention, the novel balloon dissection instrument is employed in combination with an angioscope in a manner that permits the internal visualization and treatment of tributary veins. The angioscope employed is preferably a steerable angioscope equipped with a fiber optic visualization system. The angioscope may also be equipped with other accessories, including for example, a laser delivery system for transmitting laser energy; an inflatable/deflatable balloon; a guide wire; and a tract for the transmission and delivery of irrigating agents, sclesorants, or other medicants, and the like.

In this preferred method, the apparatus may be viewed as a system utilizing an angioscope within the lumen of the vein to provide guidance and aid for the movement of the dissection instrument along the outer surface of the vein. During dissection, the two instruments are advanced in a parallel manner at about the same rate of advance, typically with the angioscope leading. As tributary veins are encountered, they are first visually detected through the angioscope. The tributary vein may then be severed and tied off, for example by means of a percutaneous incision, and the dissection process continued.

When the terminal point of the vein segment is reached, that is, when the desired length of vein segment is dissected, the vein may be severed by laser energy applied through the laser delivery system of the angioscope or by a percutaneous incision to sever the vein.

BRIEF DESCRIPTION OF THE DRAWINGS

FIG. 1 is a longitudinal cross-sectional view of the dissection instrument of the present invention.

FIG. 2 is a sectional view taken along line 2–2' of FIG. 1.

DETAILED DESCRIPTION OF THE INVENTION

Figure 3:
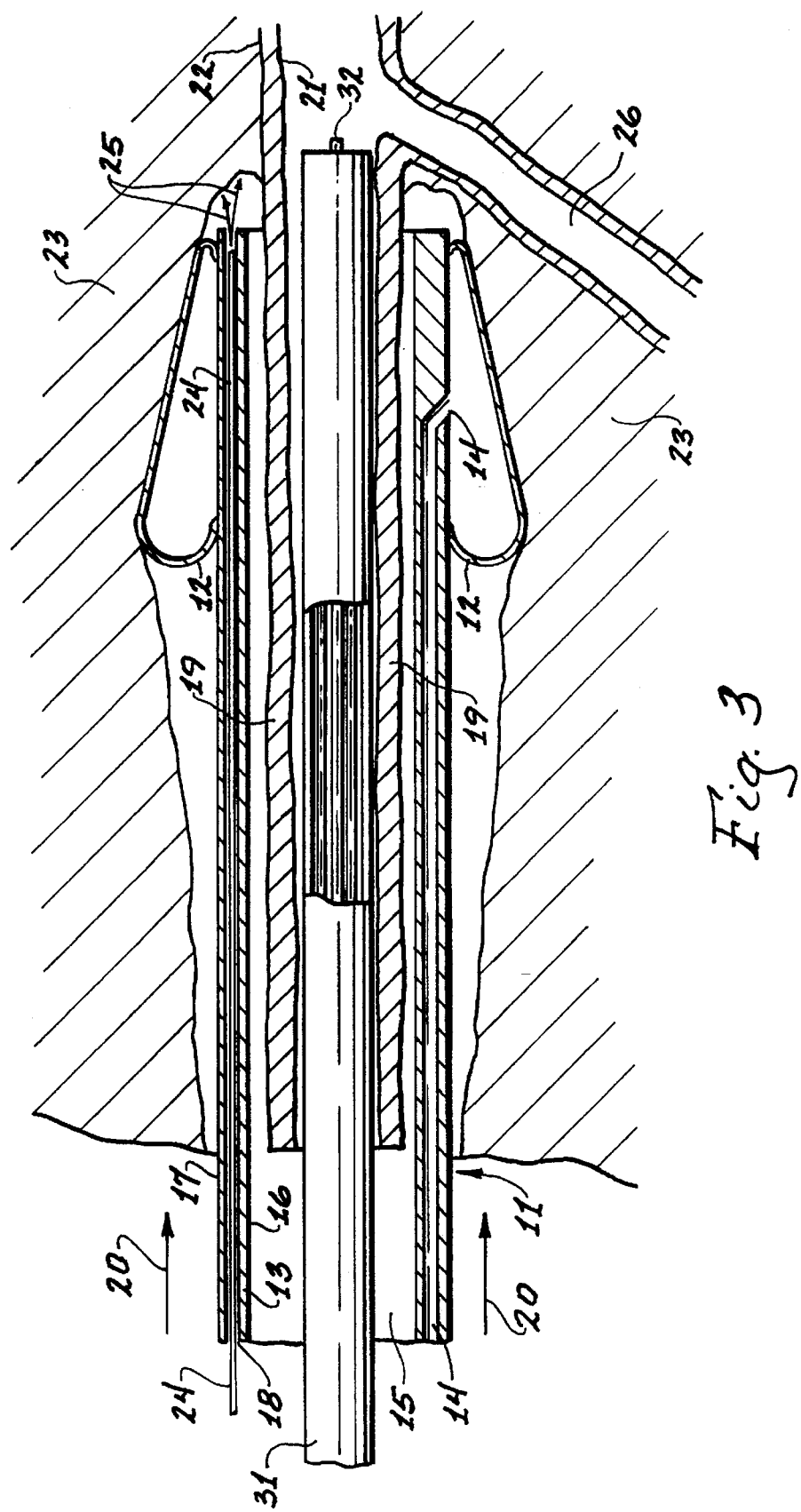
FIG. 3 is a longitudinal cross-sectional view of a dissection instrument of the present invention during its use.

FIGS. 1 and 2 illustrate a balloon dissection instrument embodying various features of the invention, including an elongated tube 11 with an inflatable/deflatable balloon element 12 attached thereto and surrounding the tube near the distal end thereof. The balloon 12 is shown in the form of a preferred embodiment wherein the shape is generally conical, with the narrow portion of the cone oriented in the direction of the distal end of the tube. Tube 11 comprises a cylindrical wall 13 having an outer surface 17 and an inner surface 16 defining a central lumen 15. One or more inflation conduits 14 extend axially within wall 13 from the proximal end of tube 11 and are in fluid communication with the interior of balloon 12. The instrument depicted in FIGS. 1 and 2 represents a preferred embodiment having at least one multi-purpose conduit(s) 18 extending axially along the length of tube 11 within wall 13 between outer surface 17 and inner surface 16, having a discharge opening at the distal end of the tube. FIG.2 illustrates a cross-section of the tube 11 of the dissection instrument taken along lines 2–2' of FIG. 1 showing wall 13 of the tube 11 having inner surface 16, outer surface 17, lumen 15, inflation conduit 14, and multi-purpose conduits 18 within wall 13.

Balloon 12 is shown in the drawings in a preferred conical shape. It will be understood however, that balloon 12 may be in different shapes, including, for example, elliptical, cylindrical, and the like. The choice of balloon shape may be made on the basis of the intended use of the instrument, for example, the type or configuration of the organ or tissues to be dissected. For example, it has been found that a balloon 12, having a rectangular cross-section is well adapted for the dissection of large areas of body tissue.

The elongated body of the dissection instrument of the invention, that is, tube 11, is preferably formed of a polymeric material, i.e. plastic material, most preferably polyurethane or polyethylene. However, if desired, tube 11 may be made of other polymeric material, including for example polypropylene, polyamide, polyethyleneterephthalate, polyimide, and the like. The invention is not limited to a particular choice of material.

Additionally, to provide lubricity and ease the movement of the instrument during use, the inner surface 16 and/or outer surface 17 of wall 13 may be coated with polytetrafluoroethylene, silicone, or other low friction coating.

The inflation conduit(s) 14, within the wall 13, are in fluid communication with the interior of balloon 12 to permit the transmission of inflating fluid from a controllable fluid source means (not shown) at the proximal end of tube 11 to the interior of the balloon near the distal end to controllably inflate the balloon 12 and in reverse flow, to permit the deflation of the balloon 12. The inflating fluid may be a liquid, such as water, or a gas such as air, $CO_2$, or the like. The controllable fluid source means may be, for example, a rubber bulb, syringe, micro pump or the like.

The method of dissection of this invention, involving the use of the novel balloon dissection instrument described hereinabove, may be visualized with the aid of FIG. 3, wherein a vein segment 19 has been partially dissected and the dissected portion thereof encompassed by tube 11 of the dissection instrument. In the drawing, vein segment 19 is characterized by an inner endothelium layer 21 and an outer layer of adventitia 22. The adventitia 22 has been separated from the surrounding fascia 23 by inflation of balloon 12 and, following deflation of the balloon 12, the instrument has been advanced in the direction shown by arrow 20, to encompass the dissected portion within lumen 15. As illustrated, the separation of the adventitia 22 and the fascia 23 by the pressure of the expanding balloon is aided by the force of a stream or jets of inert gas 25 impinging on the juncture of the adventitia and the fascia at the point of attachment. The gas is transmitted through one or more removable gasline(s), or length(s) of tubing 24 positioned within multi-purpose conduit(s) 18, from a controllable fluid supply source (not shown). Alternatively, in practice, the inert gas may be transmitted directly through the multi-purpose conduit without the use of a removable length of tubing. Furthermore, during dissection the tube 11 may be rotated in order to apply the force of the inert gas stream to the entire dissection region around the vein segment 19.

FIG. 3 further illustrates the novel use of the balloon dissection instrument of the present invention as a part of a system that includes angioscope 31 within vein segment 19, for the visualization of branching veins, such as branch 26, by means of fiber optic visualization means 32. In practice, as the balloon dissection instrument and angioscope 31 are advanced within vein segment 19, in the direction of arrow 20, and a branch, such as branch 26, is located through angioscope 31, may be severed and ligated, for example, through percutaneous incision, and the dissection continued. When the desired length of vein segment has been dissected, the vein segment may severed, for example, by means of a percutaneous incision, and the angioscope removed and the balloon dissection instrument removed with the vein segment within.

Although the present invention has been described with reference to preferred embodiments, those skilled in the art will recognize that variations may be made in form and detail without departing from the spirit and scope of the invention.

What is claimed is:

1. A method for the dissection of a blood vessel segment using a balloon dissection instrument comprising
    an elongated tube characterized by a cylindrical wall having an outer surface and an inner surface defining a central lumen, the central lumen having a diameter larger than the outer diameter of the blood vessel segment to be dissected;
    an inflatable/deflatable balloon attached to the tube, surrounding the outer surface of a distal portion of the tube;
    at least one inflation conduit extending axially along the length of the tube within the wall between the outer surface and the inner surface thereof and in fluid communication with the interior of the balloon for inflation and deflation of the balloon;
    means fluidly coupled to the inflation conduit, for inflating and deflating the balloon by controlled transmission of fluid pressure;
    said method comprising the steps of:
    a) severing a blood vessel to provide a free end of the blood vessel segment to be dissected;
    b) securing the free end;
    c) placing the distal end of the balloon dissection instrument over the free end of the segment causing the free end of the segment to enter the lumen of the dissection instrument and the distal end of the dissection instrument to be pressed between the adventitia of the blood vessel segment and the surrounding fascia;
    d) inflating the balloon to cause the adventitia and fascia to separate in the region proximate to the distal end of the dissecting instrument and provide a dissected portion of the blood vessel;
    e) deflating the balloon and advancing the instrument along the outer adventitial surface of the blood vessel to encompass the dissected portion of blood vessel segment within the lumen of the instrument;
    f) repeating the procedure of steps d) and e) and advancing the instrument until the blood vessel segment has been dissected.

2. A method according to claim 1 which additionally comprises concurrently transmitting a stream of inert gas through a conduit in the wall of the elongated tube to the distal end of the elongated tube to impinge at the juncture of the adventitia and fascia with sufficient force to separate the adventitia and fascia.

3. A method according to claim 2 wherein the blood vessel segment is a vein segment.

4. A method for the dissection of a blood vessel segment according to claim 1 which additionally comprises the concurrent use of an angioscope equipped with fiber optic visualization means, placed within the blood vessel segment, said angioscope being advanced through the blood vessel segment during dissection and serving to locate branches of said blood vessel segment.

5. A method according to claim 4 wherein said angioscope is a steerable angioscope having a proximal and a distal end comprising:
    a) an inflatable/deflatable balloon means attached to the distal end;
    b) a fiber optic means for the illumination and visualization of a region within the blood vessel at the distal end of the angioscope;
    c) means for the transmission of fluids or surgical accessory to the distal end of the angioscope.

6. A method according to claim 4 which comprises the steps of:
    a) severing the blood vessel segment at a first site to provide a free end of the blood vessel segment to be dissected;
    b) securing the free end;
    c) placing the distal end of the balloon dissection instrument over the free end of the blood vessel segment causing the segment to enter the lumen of the dissection instrument and the distal end of the dissection instrument to be pressed between the adventitia of the blood vessel segment and the surrounding fascia;
    d) inserting the angioscope through the proximal end of the balloon dissection instrument and into the free end of the blood vessel segment;
    e) advancing the angioscope through the blood vessel to visually locate a branch thereof;
    f) severing and ligating the branch;
    g) inflating the balloon to cause the adventitia and fascia to separate in the region near the distal end of the dissection instrument and provide a dissected portion of the blood vessel segment;
    h) deflating the balloon and advancing the dissection instrument along the outer adventitial surface of the blood vessel segment to encompass the dissected portion of the blood vessel segment within the lumen of the instrument;

i) advancing the angioscope by repeating steps e) and f), and advancing the dissection instrument by repeating steps g) and h), at about the same rate until the desired length of blood vessel segment has been dissected and freed from branches and is contained within the lumen of the balloon dissection instrument.

7. A method according to claim 6 wherein the blood vessel segment is a vein segment.

8. A method according to claim 7 wherein the vein segment is severed at a second site and the dissecting instrument removed with the desired vein segment therein.

9. A method for separating tissue using a balloon dissection instrument comprising:

an elongated tube characterized by a cylindrical wall having a length, an outer surface and an inner surface defining a central lumen;

an inflatable/deflatable balloon attached to the tube, surrounding the outer surface of a distal portion of the tube;

at least one inflation conduit extending axially along the length of the tube within the wall between the outer surface and the inner surface thereof and in fluid communication with the balloon for inflation and deflation of the balloon;

a means fluidly coupled to the inflation conduit, for inflating and deflating the balloon by controlled transmission of fluid pressure;

a second conduit extending axially along the length of the tube within the wall between the outer surface and the inner surface thereof having an opening at the distal end of the tube for fluid communication with the tissue for the transmission of a stream of gas therethrough;

said method comprising the steps of:

a) inserting said distal portion of said tube into said tissue;

b) introducing gas through said second conduit and simultaneously inflating said balloon to cause said tissue to separate in a region proximate to said distal end of said dissecting instrument;

c) deflating said balloon and advancing said instrument;

d) repeating steps b and c until tissue has been sufficiently separated.

10. A method according to claim 9 wherein said gas is inert gas.

11. A method according to claim 9 wherein said gas is carbon dioxide.

12. A method according to claim 9 wherein said gas is helium.

13. A method according to claim 9 wherein said gas is nitrogen.

* * * * *